US008293745B2

(12) United States Patent
Riviere et al.

(10) Patent No.: US 8,293,745 B2
(45) Date of Patent: Oct. 23, 2012

(54) USE OF IMATINIB TO TREAT LIVER DISORDERS AND VIRAL INFECTIONS

(75) Inventors: Phillippe Riviere, Saint Martin de Laye (FR); Marc Riviere, Saint Lambert (CA); Stéphanie Reader, Ste-Julie (CA)

(73) Assignee: Bioniche Life Sciences Inc., Belleville, Ontario (CA)

( * ) Notice: Subject to any disclaimer, the term of this patent is extended or adjusted under 35 U.S.C. 154(b) by 623 days.

(21) Appl. No.: 11/228,982

(22) Filed: Sep. 14, 2005

(65) Prior Publication Data
US 2006/0275260 A1 Dec. 7, 2006

Related U.S. Application Data

(63) Continuation of application No. PCT/CA2005/000869, filed on Jun. 3, 2005.

(60) Provisional application No. 60/576,573, filed on Jun. 4, 2004.

(51) Int. Cl.
*A61K 31/497* (2006.01)
*A61K 38/00* (2006.01)
*A61K 38/16* (2006.01)
(52) U.S. Cl. .............. 514/252.14; 514/21.2; 514/4.3
(58) Field of Classification Search ............. 514/252.14, 514/2
See application file for complete search history.

(56) References Cited

U.S. PATENT DOCUMENTS

| 5,843,636 A * | 12/1998 | Reyes et al. .................. 435/5 |
| 6,472,373 B1 * | 10/2002 | Albrecht .................... 514/43 |
| 6,884,804 B2 | 4/2005 | Choon-Moon ............... 514/275 |
| 7,064,127 B2 | 6/2006 | Friedman et al. ......... 514/252.18 |
| 2005/0143389 A1 | 6/2005 | Friedman et al. |

FOREIGN PATENT DOCUMENTS

| WO | WO 02/010339 A2 | 7/2002 |
| WO | WO 03/002109 A2 | 1/2003 |
| WO | WO 03/099811 A1 | 12/2003 |
| WO | WO 2005/065690 | 7/2005 |
| WO | WO 2005/072826 A2 | 8/2005 |

OTHER PUBLICATIONS

Rontana et al. "Noninvasive monitoring of patientw with chronic hepatitis C," Hepatology, 2002, vol. 36, No. 5, Suppl. 1 pp. S57-S64.*
Silini et al., "Hepatitis C Virus Infection in a Hematology Ward: Evidence for Nosocomial Transmission and Impact on Hematologic Disease Outcome"Haematologica, vol. 87 (11), pp. 1200-1208 (2002).
DeFilippis et al., "Functional Genomics in Virology and Antiviral Drug Discovery", Trends in Biotechnology, vol. 21 (10), pp. 452-457 (2003).

(Continued)

*Primary Examiner* — Shengjun Wang
(74) *Attorney, Agent, or Firm* — Winston & Strawn LLP

(57) ABSTRACT

The present invention relates to the use of imatinib for treating viral liver diseases and in particular for viral hepatitis. The invention provides the use of imatinib for inhibiting replication, transmission or both of hepatitis viruses. The invention further relates to the use of imatinib for inhibiting replication, transmission or both of other viruses including herpes virus, poxvirus, influenza virus, para influenza virus, respiratory syncytial virus, rhinovirus, yellow fever virus, west nile virus, and encephalitis virus.

23 Claims, 1 Drawing Sheet

OTHER PUBLICATIONS

Ramadori et al., "Successful Treatment of Hepatocellular Carcinoma With the Tyrosine Kinase Inhibitor Imatinib in a Patient With Liver Cirrhosis", Anti-Cancer Drugs, vol. 15, No. 4, pp. 405-409 (2004).

M. W. Bekkenk et al., EBV-Positive Cutaneous B-Cell Lymphoproliferative Disease After Imatinib Mesylate, Blood; vol. 102., No. 12. p. 4243 (2003).

Allan B. Dietz et al., Imatinib Mesylate Inhibits T-Cellproliferation In Vitro and Delayedtype Hypersensitivity In Vivo, Blood; vol. 104., No. 12. pp. 1094-1099 (2004).

Mattiuzzi et al., "Development of Varicella-Zoster Virus Infection in Patients With Chronic Myelogenous Leukemia Treated Withimatinib Mesylate", Clinical Cancer Research; vol. 9, pp. 976-980 (2003).

Supplementary European Search Report , Application No. 05752861.4, dated Aug. 13, 2010.

Copland Mhairi, et al., XP008123981, "Gastrointestinal Stromal Tumor Presenting as Hemoperitoneum in Hemophilia A", Blood, vol. 100, No. 11, pp. 99B-100B (2002).

Ohyashiki, K. et al., XP002590340, "Imatinib Mesylate-Induced Hepato-Toxicity in Chronic Myeloid Leukemia Demonstrated Focal Necrosis Resembling Acute Viral Hepatitis", Leukemia, vol. 16, No. 10, pp. 2160-2161 (2002).

James, C. et al., XP002590341, "Histological Features of Acute Hepatitis After Imatinib Mesylate Treatment", Leukemia vol. 17, No. 5, pp. 978-979, (2003).

Wassman, B. et al., XP008123966, , Clinical Activity of an ABL-Tyrosine Kinase Inhibitor (ST1571) in a Patient With CML Lymphoid Blast Crisis Relapsing After Allogeneic Stem Cell Transplantation, Blood, vol. 96, No. 11 part 2, pp. 218B (2000).

* cited by examiner

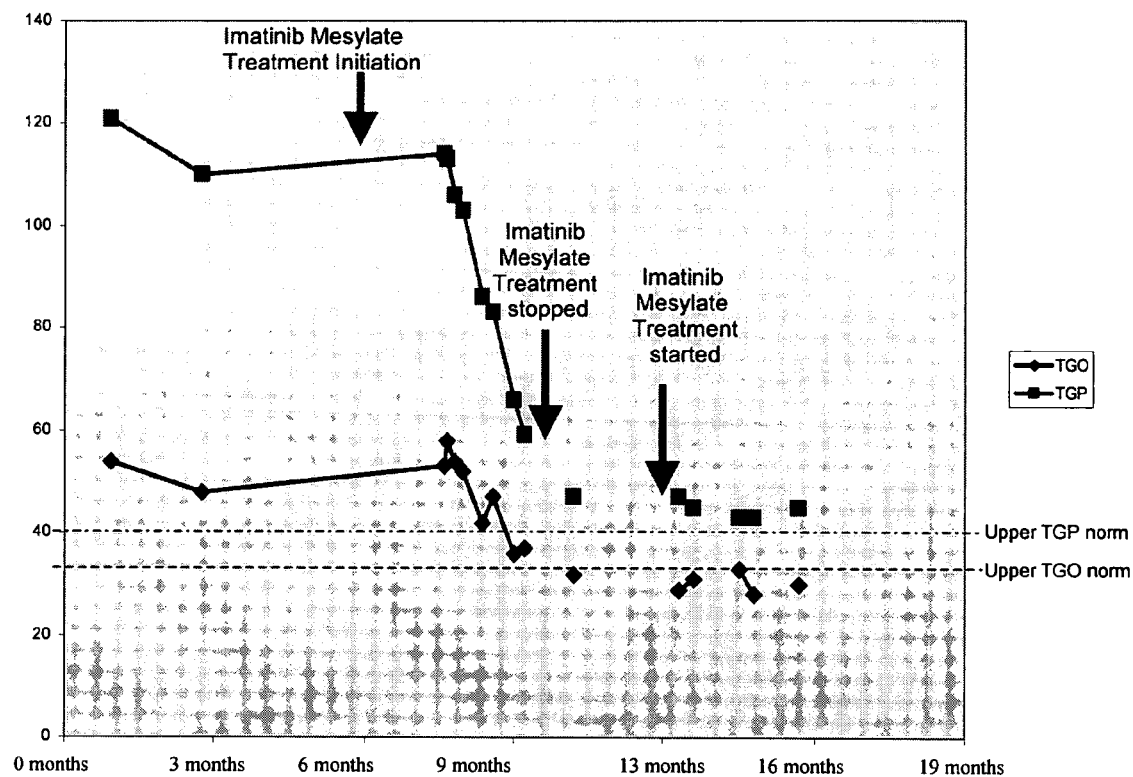

USE OF IMATINIB TO TREAT LIVER DISORDERS AND VIRAL INFECTIONS

CROSS-REFERENCE TO RELATED APPLICATIONS

This application is a continuation of International application no. PCT/CA2005/000869 filed Jun. 3, 2005, which claims the benefit of provisional application Ser. No. 60/576,573, filed Jun. 4, 2004. The entire content of each application is expressly incorporated herein by reference thereto.

FIELD OF INVENTION

The present invention relates to the use of imatinib for the treatment of liver disorders and viral infections, and in particular, the treatment of viral hepatitis.

BACKGROUND

Since its discovery in 1989, the Hepatitis C virus (HCV) has emerged as the major ethiologic agent responsible for most cases of transfusion-associated and sporadic non-A, non-B hepatitis (Heim et al., 1999; Dore et al., 2003). HCV is the causative agent of the majority of chronic disease throughout the world. An estimated 170 million persons are infected with HCV worldwide. The infection is usually persistent, and following an asymptomatic period often lasting years, many patients develop chronic liver disease, including cirrhosis and hepatocellular carcinoma.

The size of the HCV epidemic and the limited efficacy of current therapy, based on the use of interferon-alpha (INF-alpha), have stimulated intense research efforts towards the development of antiviral drugs that are both better tolerated and more effective. The most widely established strategy for developing novel anti-HCV therapeutics aims at the identification of low-molecular-weight inhibitors of essential HCV enzymes.

Current treatment of HCV infection involves combinations of IFN with ribavirin (Moll and Kohlbrenner, 2003). Although capable of apparent cures, IFN-based regimens are not effective against key viral genotypes, are poorly tolerated, and are very expensive. Vaccine development is hampered by lack of in vitro propagation systems for HCV and the high genetic variability of this single-stranded RNA virus. Several important viral targets for HCV drug development have been identified: i) the processing of viral polyprotein by virus-specific proteases; ii) viral RNA replication that uses the NS3 helicase and iii) viral NS5B RNA-dependent RNA polymerase; and viral regulatory elements such as the internal ribosomal entry site (Moll and Kohlbrenner, 2003). Recent advances in understanding the replication cycle of HCV and the determination of the crystal structures of several virally encoded enzymes have improved the prospects for development of novel therapies. Proteases and polymerases have been the focus of most drug discovery programs and compounds targeting both enzymes have now entered clinical development. However, there is no known treatment for chronic viral diseases such as HCV.

The invention now seeks to overcome disadvantages of the prior art.

SUMMARY OF INVENTION

In a first aspect of the invention, provided is a use of imatinib or a pharmaceutically acceptable salt thereof, in a method for treating or preventing a viral liver disorder.

In a second aspect of the invention, provided is a use of imatinib or a pharmaceutically acceptable salt thereof, in a method for inhibiting replication, transmission or both of a hepatitis virus.

In a third aspect of the invention, provided is a method of treating a patient infected with a hepatitis virus comprising administering a therapeutically effective amount of imatinib or a pharmaceutical salt thereof to the patient. In an embodiment of the invention, the hepatitis virus is HAV, HBV, HCV, HDV, HEV, a non-A non-E (NANE) hepatitis virus, HGV, TTV, or SENV.

In a fourth aspect of the invention, provided is use of imatinib or a pharmaceutically acceptable salt thereof, in a method for decreasing liver enzyme level in a patient. In an embodiment of the invention, the liver enzyme is a transaminase.

In a fifth aspect of the invention, provided is a use of imatinib or a pharmaceutically acceptable salt thereof, in a method for inhibiting replication or transmission of a herpes virus. In an embodiment of the invention, the herpes virus is HSV-1, HSV-2, VZV, HCMV, HHV-6, HHV-7, EBV, or HHV-8.

In a sixth aspect of the invention, provided is a use of imatinib or a pharmaceutical salt thereof, in a method for inhibiting replication or transmission of a poxvirus. In this embodiment, the poxvirus is an orthopoxvirus, parapoxvirus, avipoxvirus, capripoxvirus, leporipoxvirus, suipoxvirus, molluscipoxvirus, yatapoxvirus, or entomopoxvirus.

In a seventh aspect of the invention, provided is a use of imatinib or a pharmaceutically acceptable salt thereof, in a method for inhibiting replication or transmission of a RNA virus selected from a group consisting of: influenza virus, parainfluenza virus, respiratory syncytial virus, rhinovirus, yellow fever virus, west nile virus, and encephalitis virus.

In a eighth aspect of the invention, provided is a use of a receptor protein kinase inhibitor in a method for inhibiting replication or transmission of a hepatitis virus.

This summary of the invention does not necessarily describe all necessary features of the invention but that the invention may also reside in a sub-combination of the described features.

BRIEF DESCRIPTION OF THE FIGURES

These and other features of the invention will become more apparent from the following description in which reference is made to the appended drawings wherein:

FIG. 1 is a line graph illustrating the effect of imatinib mesylate treatment on glutamic oxaloacetic transaminase (TGO) and glutamic pyruvate transaminase (TGP) levels in a patient or subject.

DETAILED DESCRIPTION OF THE PREFERRED EMBODIMENTS

The following description is of a preferred embodiment by way of example only and without limitation to the combination of features necessary for carrying the invention into effect.

Imatinib (4-[(4-methyl-1-piperazinyl)methyl]-N-[4-methyl-3-[[4-(3-pyridinyl)-2-pyrimidinyl]amino]phenyl]-benzamide) and its methanesulfonate derivative, imatinib mesylate (formerly known as STI571; trademarked as Gleevec in the United States and Glivec in Europe), are protein-tyrosine kinase inhibitors selective for Bcr-Abl tyrosine kinase. Imatinib is also a specific inhibitor of c-Kit tyrosine kinase activity and is equally effective against both wild-type and constitutively active enzyme (Radford IR, 2002). The Kit receptor tyrosine kinase is expressed by practically all gastrointestinal stromal tumors (GIST), and gain-of-function mutation of c-kit is present in most GISTs (Kitamura et al., 2003). GIST is the most common mesenchymal tumor of the human gastrointestinal tract. Imatinib has proven to be remarkably effective in heavily pre-treated patients with advanced GIST. Imatinib is currently being investigated for use in the treatment of chronic myeloid leukemia (CML), acute myeloid leukemia (AML), acute lymphoblastic leukemia (ALL), myelodysplastic syndrome (MDS), ovarian cancer, prostrate cancer, soft tissue sarcoma, and malignant glioma (Novartis Drug Record for Gleevec, T2004-10, 89019002, January 2004).

However, imatinib has side effects and been shown to cause hepatoxicity as evidenced by elevated liver enzymes (transaminases, alkaline phosphatase). Liver toxicity characterized by severe elevation of transaminases or bilirubin occured in 3 to 12% of patients in the Novartis clinical trial and was managed with dose reduction or interruption. Grade 3 or higher adverse events occurred in 21.1% of GIST patients treated with 400 vs 600 mg imatinib. Severe hepatoxicity has been reported in some CML patients (James et al. Leukemia. 2003 May; 17(5) 978-9). James et al. have reported two cases of hepatitis occurring during the treatment of CML with imatinib mesylate. In both cases, transaminases levels were severely elevated. In one case, histological examination showed lesions that appeared to be viral hepatitis induced. After stopping the treatment, liver samples were tested for Hepatitis A, B and C as well as CMV, EBV and herpes virus. The results were negative. In both cases, transaminase levels returned to normal following the discontinuation of treatment.

Surprisingly, the present invention has indicated that imatinib, and in particular its methanesulfonate derivative, imatinib mesylate, are effective for treating viral liver diseases, for example, but not limited to viral hepatitis, and in particular hepatitis C. As provided herein, imatinib treatment is effective for ameliorating viral hepatitis, for example, but not limited to, by decreasing liver enzyme levels, maintaining or decreasing viral load, maintaining or decreasing RNA viral load, maintaining or decreasing HCV (E1A-2) or a combination thereof. In particular, the present invention has demonstrated that the administration of imatinib to a human subject diagnosed with hepatitis c virus is capable of lowering liver enzyme transaminase levels to within about normal ranges. Further, the present invention has demonstrated that the administration of imatinib to a human subject diagnosed with hepatitis virus resulted in a clear improvement in the quality of the subject's life.

While the invention is not meant to be limited to any particular mechanism of action or bound by theory, it is believed that the antiviral properties of imatinib may be due in part to its ability to inhibit viral replication and transmission. It is known that cellular signal transduction pathways play an important role in viral infection and that cellular phosphorylation events during viral infection are necessary for effective viral replication and proliferation (Muthumani et al, 2004). However, little is known about which particular cellular signaling pathways are crucial for viral replication.

Numerous cellular signaling pathways have been investigated in connection with viral replication. For example, Hirasawa et al have investigated the role of mitogen-actived protein kinases (MAPKs) in the regulation of encephalomyocarditis virus (EMC) (Hirasawa et al., 2003, J, Virol. 77, pp. 5649-5656). MAPK is a family of serine threonine kinases which are activated via receptor tyrosine kinases and are central components in the signal transduction pathways involved in the regulation of cell proliferation. Hirasawa et al examined the phosphorylation of MAPKs, including extracellular signal-regulated kinase (ERK1\2), p38 MAPK, and stress-activated protein kinase 1\c-jun NH2-terminal kinase (SAPK\JNK) in EMC virus-infected L929 cells (Hirasawa et al., 2003). They found that p38 MAPK and SAPK-JNK, but not ERK1\2 were activated during viral infection. Hirasawa et al. also examined the effect of these kinases on the replication of EMC virus in L929 cells by using specific inhibitors including genistein or herbimycin A for tyrosine kinase inhibitor. They found that tyrosine kinase inhibitors suppressed viral replication and that the inhibitory effect was primarily on viral protein synthesis. On the basis of their observations, they conclude that p38 MAPK plays a critical role in the replication of EMC virus, probably in the translation of viral RNA (Hirasawa et al., 2003). Muthumani et al. also studied the bioactivity of serine-threonine protein kinase p38 inhibitor RWJ67657 against HIV-1 infection. Inhibition of the p38 pathway by RWJ67657 inhibitor was effective in inhibiting HIV-1 replication (Muthumani et al., 2004, AIDS, 18, pp. 739-748).

Again, without wishing to be bound by theory or limiting in any manner, the results obtained in respect of the present invention suggest that replication and transmission of hepatitis viruses involve one or more protein targets which are capable of being modulated by imatinib. It is possible that imatinib may target one or more receptor tyrosine kinases and that inhibition of these kinases is correlated with decreased viral replication and transmission. The effectiveness of imatinib for the treatment of viral hepatitis may be due in part to alterations in hepatocyte signaling pathways which are involved in regulation of cell death and protein production, for example, but not limited to transaminases.

The present invention provides the use of a receptor tyrosine kinase inhibitor, and in particular, imatinib or a pharmaceutically acceptable salt thereof, in a method for treating or preventing a viral liver disease, and in particular viral hepatitis, in a patient. In an embodiment of the present invention, which is not meant to be limiting, there is provided the use of imatinib for inhibiting replication, transmission or both replication and transmission of hepatitis viruses. The invention contemplates the use of receptor tyrosine kinase inhibitors such as imatinib, for treating viral liver disorders in animal patients, preferably mammalian patients, and even more preferably human patients.

As used herein, the term "imatinib" includes isomers, derivatives and metabolites of 4-[(4-methyl-1-piperazinyl) methyl]-N-[4-methyl-3-[[4-(3-pyridinyl)-2-pyrimidinyl] amino]phenyl]-benzamide, said isomers, derivatives and metabolites of imatinib having therapeutic properties similar to the parent imatinib compound. Examples of such isomers, derivatives, and metabolites include, but is not limited to: imatinib mesylate (4-[(4-methyl-1-piperazinyl)methyl]-N-[4-methyl-3-[[4-(3-pyridinyl)-2-pyrimidinyl]amino]phenyl]-benzamide methanesulfonate) and imatinib metabolite CGP74588.

As employed herein, the term "subject" is used interchangeably with the term "patient". Neither term is meant to limit the scope of the present invention.

The present invention further contemplates combination therapies for treating viral liver disorders, for example, but not limited to hepatitis C viral infections. For example, tyrosine kinase inhibitors which may be used include inhibitors to epidermal growth factor receptors (EGFR) such as monoclonal antibodies and small-molecule inhibitors. EGFR inhibitors including monoclonal antibodies, such as Trastuzumab (Herceptin), IMC-C225 (Cetuximab) and others (ABX-EGF, EMD 72000), and tyrosine-kinase inhibitors, such as ZD1839 (Gefitinib, Iressa), OSI-774 (Erlotinib, Tarceva) and others (CI-1033, GW2016), may be employed as a combination therapy with imatinib. Monoclonal antibodies may block ligand binding to the extracellular domain, whereas the small-molecule inhibitors may exert their effects at the intracellular portion of the receptor to prevent tyrosine kinase phosphorylation and subsequent activation of signal transduction pathways.

The present invention provides for the use of imatinib in a method to treat a subject or patient infected with a hepatitis virus, for example, but not limited to HCV, HAV, HBV, HDV, and HEV. In a specific embodiment, the present invention provides for the use of imatinib to treat a subject or patient infected with HCV. In an alternate embodiment, the invention contemplates the use of imatinib for treating a subject or patient infected with a non-A non-E (NANE) hepatitis virus, also referred to as hepatitis-like viruses. Non-limiting examples of non-A non-E or hepatitis-like viruses include: HGV, TT virus (TTV) and SEN virus.

The use of imatinib in a subject infected with a hepatitis virus, or in a method for the treatment of a subject infected with a hepatitis virus with imatinib results in an improvement in at least one indicator of viral infection, disease state or disease progression. For example, but not to be considered limiting, the use of imatinib may result in a reduction of viral load, an inhibition of viral replication, an inhibition of viral transmission, a reduction in the level of one or more hepatic enzymes or liver-associated products as described herein, a positive change in hepatic histology, as for example demonstrated by biopsy, or a combination thereof. Further, the use of imitinib may result in a qualitative improvement, for example, an improvement in the general quality of life of the subject. In this regard, but without wishing to be limiting, a qualitative improvement may be characterized by less fatigue, sickness, or an increased ability to carry out normal daily activities.

It is also contemplated that the improvement in at least one indicator of viral infection, disease state or disease progression may comprise maintaining viral load. In such an embodiment, the maintenance of viral load, rather than an increase in viral load may be indicative of an improvement to a person of skill in the art.

The invention also provides a method of treating a patient infected with a virus responsive to imatinib treatment. The invention further provides a method of treating a subject or patient having compromised liver function such as elevated liver enzyme levels. In a preferred embodiment of the invention, the method of treatment encompassed by the invention is directed to the treatment of a mammalian patient in need thereof. In a further preferred embodiment of the invention, the patient is a human patient.

In one aspect, the invention provides a method of treating a subject or patient infected with a hepatitis virus or hepatitis-like virus (see the examples set out above) comprising administering a therapeutically effective amount of imatinib or a pharmaceutically acceptable salt thereof.

In an alternate embodiment, the invention provides a method of treating a subject or patient infected with a hepatitis virus or hepatitis-like virus (see the examples set out above) comprising the steps of a) administering a therapeutically effective amount of imatinib or a pharmaceutically acceptable salt thereof, and b) monitoring the effect of the administering step at one or more times thereafter.

The present invention also provides a method of treating a subject infected with a hepatitis virus or hepatitis-like virus comprising the steps of a) testing a subject to determine if the subject is infected with a hepatitis virus or hepatitis-like virus and b) administering imatinib in a dosage regimen to treat the subject or patient infected with the virus.

In a specific embodiment, the present invention provides a method of treating a subject infected with HCV comprising the steps of a) testing a subject to determine if the subject is infected with HCV and b) administering imatinib in a dosage regimen to treat the patient.

Various tests are known in the art to determining if a subject is infected with a hepatitis virus and any such test known in the art may be employed by the present invention.

In a further aspect, the invention provides the use of imatinib for decreasing one or more liver enzyme levels and other products in a patient. In a preferred embodiment of the invention, the liver enzyme comprises one or more transaminases, for example, but not limited to alanine transaminase, aspartate transaminase or both. Other products and enzymes that are indicative of liver function include, but are not limited to bilirubin, alkaline phosphatase, creatine and soluble cytochrome c. Soluble cytochrome c is a clinical marker of apoptosis in patients with liver disease. As shown by Ben-Ari Z et al. 2003, untreated patients with chronic viral hepatitis (B and C) had significantly higher levels (mean 282.8+/−304.3 ngxmL(−1)) than treated patients (77.9+/−35.8 ngxmL(−1); P=0.001). Soluble cytochrome c levels are increased in different types of liver disease. Soluble cytochrome c is probably derived from the liver and secreted into the bile. Levels correlate with the apoptotic index and are affected by antiviral treatment. Soluble cytochrome c may serve as a serum marker of apoptosis.

The precise dose or dosage regimen of imanitib or its pharmaceutically acceptable salt will depend on a number of factors which will be apparent to those skilled in the art and in light of the disclosure herein. In particular these factors include: the formulation, the route of administration employed, the patient's species, gender, age, and weight, and the severity and type of the condition being treated. Methods for determining dosage and toxicity are well known in the art with studies generally beginning in animals and then in humans if no significant animal toxicity is observed. The appropriateness of the dosage can be assessed by monitoring liver function including transaminases, bilirubin, alkaline phosphatase, soluble cytochrome c analysis, HCV antibodies (EIA-2) and by monitoring viral load. Generally, it is preferred that a patient treated or undergoing therapy be monitored for signs of adverse drug reactions and toxicity, especially with regard to liver and renal function.

In some circumstances, it may be desirable to combine imatinib treatment with one or more additional drugs for the treatment of viral hepatitis and optionally associated conditions. For example, it may be desirable to combine imatinib mesylate treatment with an interferon such as interferon alpha-2a, interferon alpha-2b, and pegylated derivatives thereof. It may also be desirable to combine imatinib mesylated treatment with ribavirin and/or other anti-hepatitis drugs. It is further contemplated that imatinib treatment may precede or follow, or both precede and follow treatment of a patient with one or more other drugs, for example, but not limited to an interferon or the like. Thus, in an embodiment of the present invention, which is not meant to be limiting in any manner, there is provided a method of treating a patient infected with hepatitis virus comprising the steps of a) administering one or more drugs to a patient and subsequently b) administering imatinib or a pharmaceutically acceptable salt thereof to a patient alone, or in combination with one or more additional drugs. In an embodiment of the present invention, which is not meant to be limiting in any manner, a patient infected with hepatitis virus is administered interferon beta, interferon alpha, ribavirin, pegylated interferon, or a combination thereof. This treatment is subsequently followed by administering imatinib or a pharmaceutically acceptable salt thereof.

Where the patient is human, the therapeutic dosage of imatinib, and more preferably, imatinib mesylate, will generally be between 50 mg and 1000 mg/day, more preferably 100 mg to 1000 mg/day depending on the severity of the condition and whether the imatinib is administered alone or in combination with other drugs. However, the present invention contemplate daily doses of 50 mg, 75 mg, 100 mg, 200 mg, 200 mg, 250 mg, 300 mg, 400 mg, 500 mg, 600 mg, 700 mg, 800 mg, 900 mg and 1000 mg. Further, the daily dosage may be defined by a range of any of the values listed above. Preferably, the dosage of imatinib is between 400 mg/day and 600 mg/day for adults. It has been reported that high-dose imatinib (more than 600 mg) was well tolerated but resulted in more frequent myelosuppression. High-dose imatinib induced higher rates of complete cytogenetic response and of molecular response in patients with newly diagnosed chronic phase CML (Kantarjian H, et al., Blood. 2004). The preferred dosage of imatinib for children is between 200 mg/m$^2$/day and 400 mg/m$^2$/day, preferably 260 mg/m$^2$/day and 360 mg/m$^2$/day. However, dosages of 220 mg/m$^2$/day, 250 mg/m$^2$/day, 300 mg/m$^2$/day, 350 mg/m$^2$/day or any range defined by the values listed above may be employed in the present invention.

Imatinib may be delivered to a subject or patient through any suitable route, as would be known to a person of skill in the art although oral administration is preferable. More preferably, the prescribed dose is administered orally with a meal and a large glass of water. Doses of 400 mg or 600 mg are preferably administered once daily, whereas a dose of 800 mg is preferably administered as 400 mg twice a day. However, amount and frequency is not meant to be limiting in any manner. In this regard, the present invention contemplates that imatinib may be delivered once, twice, three, four or five times a day or more.

It is preferred that imatinib is formulated into an appropriate dosage form for oral adminstration to a patient or subject. Any dosage form which is suitable for oral administration of imatinib may be employed in the methods and uses of the present invention as described herein. In a preferred embodiment, imatinib is formulated into a tablet or capsule, for example, but not limited to a film coated tablet.

For patients unable to swallow a film-coated tablet, the tablet may be dispersed in a glass of water or apple juice. In such a case, the required number of tablets can be placed in an appropriate volume of beverage (for example, but not limited to approximately 50 ml for a 100 mg tablet, and 200 ml for a 400 mg tablet) and stirred with a spoon. The suspension is preferably administered immediately after complete disintegration of the tablet(s).

In addition to being effective as anti-viral agent for hepatitis viruses, the invention provides the use of imatinib for inhibiting the replication and transmission of other DNA and RNA viruses. The invention provides the use of imatinib for inhibiting replication and transmission of herpes, pox, and certain RNA viruses in a patient. The patient may be an animal and more preferably a mammal. Even more preferably, the patient is a human.

In an alternate embodiment, the present invention provides the use of imatinib for inhibiting replication, transmission or both replication and transmission of herpes viruses such as, but not limited to: HSV-1, HSV-2, VZV, HCMV, HHV-6, HHV-7, EBV, and HHV-8.

While the invention is not meant to be bound by theory or limited to any particular mechanism of action, it is believed that the imatinib interferes with herpes virus replication, transmission or both. Tyrosine phosphorylation events have been implicated in the early stages of herpes virus interaction with host cells. For example, HHV-8 has been reported to induced integrin-dependent focal adhesion kinase (FAK). Activation of FAK is thought to be a critical step which is responsible for subsequent phosphorylation of other cellular kinases, cytoskeletal rearrangements, and other functions important for virus-host cell interaction and eventual cell infection (Sharma-Walia et al., J. Virol. 2004, 78(8), pp. 4207-4223). It is suggested that imatinib, while being selective for Bcr-Abl and c-Kit tyrosine kinases, is capable of inhibiting kinases such as FAK which are responsible for phosphorylation events essential for herpes virus replication and transmission.

It is further believed that imatinib overcomes the herpes virus mediated inhibition of the interferon signaling pathway and thereby restores the immune response triggered by a herpes infection. HSV-1 has been shown to inhibit the interferon signaling pathway at several sites (Chee and Roizman, 2004, J. Virol. 78(8), 4185-4196). Yokota et al (J. Virol., 2004, 78(12), 6282-6286) showed that the HSV-1 inhibited IFN induced phosphorylation of Janus kinases (JAK) in infected cells. It is believed that imatinib is capable of both reducing viral load and enhancing immune function in patients infected with a herpes virus.

The invention further provides the use of imatinib for inhibiting replication, transmission or both replication and transmission and of a poxvirus in a patient. Poxviruses which may be inhibited using imatinib include, but are not limited to: orthopoxviruses, parapoxviruses, avipoxviruses, capripoxviruses, leporipoxviruses, suipoxviruses, molluscipoxviruses, yatapoxviruses, and entomopoxviruses.

It is known that a variety of phosphorylation events are involved in the infection, replication and pathogenesis of poxviruses. Masters et al., (J. Biol. Chem. (2001), 256(51), pp. 48371-48375) reported the activation of the rapid induction of multiple intracellular phosphorylation events following adsorption of the myxoma virus, a member of the Leporipoxvirus genus. These phosphorylation events were reported to affect the ultimate level of myxoma virus replication. Frischknecht et al. (Nature, 1999, 401(6756), pp. 926-929) suggested that the vaccinia virus spreads between cells by mimicking the tyrosine receptor kinase signalling pathways which are normally involved in actin polymerization at the plasma membrane. Phosphorylation of tyrosine 112 in the viral protein A36R by Src family kinases was reported to be essential for actin-based motility of vaccinia. Tzahar et al. (EMBO Journal, 1998, 17(20), pp. 5948-5963) suggested that the virulence of poxviruses was dependent on virus encoded growth factors which interact with the Erb receptor protein kinases. The viral growth factors were found to induce sustained MAPK activation resulting in enhanced cell proliferation. The authors suggested that signal potentiation and targeting to specific receptor combinations contribute to cell transformation at specific sites of poxvirus infection.

Again, while the present invention is not limited to any particular mechanism of action, it is believed that imatinib's effectiveness in combating poxvirus infections is due at least in part, to the inhibition of tyrosine phosphorylation events essential to pox virus replication and transmission. Imatinib's effectiveness in combating pox virus infections does not appear to be limited to its selective inhibtion of Brc-Abl and c-Kit tyrosine kinases.

The invention further provides the use of imatinib for inhibiting replication and transmission of a RNA virus (but not HIV) in a patient. The invention encompasses the use imatinib for inhibiting replication and transmission of RNA viruses such as (but not including HIV) influenza virus, parainfluenza virus, respiratory synctial virus, rhinovirus, yellow fever virus, west nile virus, and encephalitis virus.

The invention also provides methods of treating a patient suffering an infection with any of the herpes, pox, and RNA viruses discussed above, comprising administering a therapeutically effective amount of imatnib, and in a preferred embodiment, a therapeutically effective amount of imatinib mesylate. As discussed above, the precise dosage of imatinib or its derivative imatinib mesylate will depend on numerous factors and can be determined using methods known in the art.

The above description is not intended to limit the claimed invention in any manner, furthermore, the discussed combination of features might not be absolutely necessary for the inventive solution.

EXAMPLES

The present invention will be further illustrated in the following examples. However it is to be understood that these examples are for illustrative purposes only, and should not be used to limit the scope of the present invention in any manner.

Example One

Effect on Imatnib Mesylate Treatment in a Patient Suffering GIST and HCV

A 57 year old male diagnosed with chronic active hepatitis C. Laboratory testing reveled elevated aspartate and alanine aminotransaminases (AST\ALT) levels indicating liver injury. The patient was positive for antibodies for HCV. Histological confirmation of chronic hepatitis was corroborated by positive hepatic biopsies at month zero.

For 18 months, the patient was treated with interferon alpha-2 at 180 µg/week. For the next 4 months, the patient was given intravenous administration of 6 million units (MU) interferon-beta daily for 6 weeks followed by three times weekly for 20 weeks. Subsequently, the patient was treated with interferon alpha-2 at 180 µg/week plus ribavirin 1000-1200 mg/day for 5 months. Subsequently, the patient was treated with pegylated interferon alpha-2b (PEG-interferon) at 1.5 µg/kg once weekly for 25 months. The latter treatment was stopped in October 2002. During all these treatments, the patient had prolonged elevated aminotransferases and a poor quality of life, including extreme fatigue, sickness and was unable to work. None of the treatments received for HCV improved the enzymatic situation of the patient or the hepatic histology as demonstrated by biopsies. The chronic hepatitis was qualified as stable.

Subsequently, the patient was diagnosed with a GIST of the posterior wall of the stomach. The patient was treated with 400 mg/day of imatinib mesylate in a 5-month period. The patient was treated with 400 mg/day of imatinib mesylate preoperatively for 5 months. The patient suffered acute abdominal pain at this time, wherein upon treatment was halted upon diagnosis of acute hemorrhage of the tumor, a known complication of the treatment of such GIST with imatinib mesylate. The patient then underwent surgical resection of the GIST. Imatinib mesylate treatment was reinitiated postoperatively. The patient responded well to imatinib mesylate treatment and achieved cytogenetic and molecular remission of his GIST with treatment of imatinib mesylate. The size and attenuation of the gastric tumor were measured by histologic examination with the tumor showing significant decreased attenuation after imatinib mesylate treatment. The patient reported a clear improvement of his quality of life and was able to go back to a normal professional life similar to his status prior to the diagnosis of his hepatitis C. The patient is in a good condition without metastasis one year after the initiation of the imatinib mesylate treatment. The hepatic function of the patient was monitored on a weekly basis during the imatinib mesylate treatment. Within 2 weeks after the beginning of imatinib mesylate treatment, the patient's levels of aspartate aminotransferase and alanine aminotransferase were dramatically decreased (see FIG. 1). The patient's liver function returned to about normal activity with continued treatment with imatinib mesylate (see FIG. 1).

All citations are herein incorporated by reference.

The present invention has been described with regard to preferred embodiments. However, it will be obvious to persons skilled in the art that a number of variations and modifications can be made without departing from the scope of the invention as described herein.

What is claimed is:

1. A method for treating a patient having a liver disorder, which comprises:
    diagnosing whether the patient is infected with a hepatitis virus, wherein the patient is treated with imatinib based on positive evidence from a diagnostic test confirming that the patient is infected with a hepatitis virus;
    administering to the virus-infected patient a therapeutically effective amount of imatinib or a pharmaceutically acceptable salt thereof to return the liver function of the patient to about normal level so as to treat the patient; and
    monitoring the effect of the administering step at one or more times thereafter.

2. The method according to claim 1, wherein the imatinib salt is imatinib mesylate.

3. The method according to claim 1, wherein the patient is an animal.

4. The method according to claim 3, wherein the animal is a mammal.

5. The method according to claim 1, wherein the patient is a human.

6. The method according to claim 1, wherein the virus is HCV, HAV, HBV, HDV or HEV.

7. The method according to claim 1, wherein the virus is a non-A non-E (NANE) hepatitis virus.

8. A method for treating a patient infected with a hepatitis virus, which comprises administering to the patient a therapeutically effective amount of imatinib or a pharmaceutically acceptable salt thereof based on positive evidence from a diagnostic test confirming that the patient is infected with a hepatitis virus to return the liver function of the patient to about normal level so as to treat the patient.

9. The method according to claim 8, wherein the virus is HCV, HAV, HBV, HDV, or HEV.

10. The method according to claim 8, wherein the virus is a non-A non-E (NANE) hepatitis virus.

11. The method of claim 1, wherein the diagnostic test is an antibody test for HCV.

12. A method for treating a patient having a liver disorder, which comprises:

diagnosing whether the patient is infected with a hepatitis virus, wherein the patient is treated with imatinib based on positive evidence from a diagnostic test confirming that the patient is infected with a hepatitis virus; administering to the virus-infected patient a therapeutically effective amount of imatinib or a pharmaceutically acceptable salt thereof to return the liver function of the patient to about normal level so as to treat the patient; and monitoring the effect of the administering step at one or more times thereafter, and which further comprises the co-administration of an interferon.

13. The method according to claim 12, wherein the interferon is selected from a group consisting of: interferon alpha-2a, interferon alpha-2b, and pegylated derivatives thereof.

14. The method according to claim 12, wherein the imatinib salt is imatinib mesylate.

15. The method according to claim 14, wherein the amount of imatinib mesylate is between 100 mg/day and 1000 mg/day.

16. The method according to claim 14, wherein the amount of imatinib mesylate is between 400 mg/day and 600 mg/day.

17. The method according to claim 14, wherein the amount of imatinib mesylate is 400 mg/day.

18. The method according to claim 14, wherein the amount of imatinib mesylate is between 260 mg/m$^2$/day and 360 mg/m$^2$/day.

19. A method for treating a patient infected with a hepatitis virus, which comprises administering to the patient a therapeutically effective amount of imatinib or a pharmaceutically acceptable salt thereof based on positive evidence from a diagnostic test confirming that the patient is infected with a hepatitis virus to return the liver function of the patient to about normal level so as to treat the patient, and which further comprises the co-administration of an interferon selected from a group consisting of: interferon alpha-2a, interferon alpha-2b, and pegylated derivatives thereof.

20. The method according to claim 19, wherein the imatinib salt is imatinib mesylate.

21. The method according to claim 20, wherein the amount of imatinib mesylate is between 100 mg/day and 1000 mg/day.

22. A method for treating a patient having a liver disorder, which comprises:

diagnosing whether the patient is infected with a hepatitis virus, wherein the patient is treated with imatinib based on positive evidence from a diagnostic test confirming that the patient is infected with a hepatitis virus;

administering to the virus-infected patient a therapeutically effective amount of imatinib or a pharmaceutically acceptable salt thereof to return the liver function of the patient to about normal level so as to treat the patient; and monitoring the effect of the administering step at one or more times thereafter, and wherein, for the time before said administering and during said administering, the patient is diagnosed with a liver disorder selected from the group consisting of hepatitis C virus infections.

23. The method of claim 22 wherein during said method, the patient is tested with one or more diagnostic tests selected from the group consisting of a) one or more tests to determine if the patient is infected with hepatitis C virus and b) one or more liver enzyme tests.

* * * * *